(12) United States Patent
Anton (10) Patent No.: US 9,901,439 B2
(45) Date of Patent: Feb. 27, 2018

(54) GORE-TEX COVERED BREAST IMPLANTS TO MINIMIZE CAPSULAR REACTION AND INFECTION WHILE REDUCING PALPABILITY

(71) Applicant: Mark A. Anton, Newport Beach, CA (US)

(72) Inventor: Mark A. Anton, Newport Beach, CA (US)

( * ) Notice: Subject to any disclaimer, the term of this patent is extended or adjusted under 35 U.S.C. 154(b) by 28 days.

(21) Appl. No.: 14/876,754

(22) Filed: Oct. 6, 2015

(65) Prior Publication Data

US 2016/0095696 A1   Apr. 7, 2016

Related U.S. Application Data

(60) Provisional application No. 62/066,704, filed on Oct. 21, 2014, provisional application No. 62/060,480, filed on Oct. 6, 2014.

(51) Int. Cl.
*A61F 2/12* (2006.01)
*A61L 27/16* (2006.01)
*A61L 27/18* (2006.01)
*A61L 27/34* (2006.01)

(52) U.S. Cl.
CPC ............. *A61F 2/12* (2013.01); *A61L 27/16* (2013.01); *A61L 27/18* (2013.01); *A61L 27/34* (2013.01); *A61F 2210/0076* (2013.01); *A61F 2220/005* (2013.01); *A61F 2310/00389* (2013.01); *A61L 2430/04* (2013.01)

(58) Field of Classification Search
CPC ...................................................... A61F 2/12
USPC ............................................................ 623/7–8
See application file for complete search history.

(56) References Cited

U.S. PATENT DOCUMENTS

| | | | |
|---|---|---|---|
| 3,366,975 A * | 2/1968 | Pangman ............ | A61F 2/12 128/DIG. 21 |
| 4,820,303 A | 4/1989 | Brauman | |
| 5,770,734 A | 6/1998 | Sabb | |
| 5,779,734 A | 7/1998 | Ledergerber | |
| 6,432,138 B1 * | 8/2002 | Offray .............. | A61F 2/12 623/8 |
| 8,372,423 B2 | 2/2013 | Marshall et al. | |
| 8,647,393 B2 | 2/2014 | Marshall et al. | |
| 2009/0024228 A1 * | 1/2009 | Lesh ................ | A61F 2/0059 623/23.72 |
| 2009/0198333 A1 * | 8/2009 | Becker ............. | A61F 2/0077 623/8 |
| 2009/0254179 A1 * | 10/2009 | Burnett ............. | A61B 5/076 623/8 |
| 2011/0270391 A1 * | 11/2011 | Chitre .............. | A61F 2/12 623/8 |

(Continued)

FOREIGN PATENT DOCUMENTS

WO   WO 2014/116490 A1   7/2014

OTHER PUBLICATIONS

WO, PCT/US2015/054320 ISR and Written Opinion, dated Dec. 29, 2015.

(Continued)

*Primary Examiner* — Suzette J Gherbi
(74) *Attorney, Agent, or Firm* — One LLP; Joseph K. Liu (57) ABSTRACT

This invention relates generally to a breast implant having an ePTFE layer, a Silicone layer of a breast implant core, and an interface between the ePTFE layer and the Silicone layer.

17 Claims, 5 Drawing Sheets

(56) References Cited

U.S. PATENT DOCUMENTS

| | | | |
|---|---|---|---|
| 2013/0190870 A1* | 7/2013 | Padsalgikar | A61L 27/18 623/8 |
| 2015/0250582 A1* | 9/2015 | Greenhalgh | A61F 2/12 623/8 |
| 2016/0095696 A1* | 4/2016 | Anton | A61L 27/16 623/8 |
| 2017/0020657 A1* | 1/2017 | Schuessler | A61F 2/12 |

OTHER PUBLICATIONS

Berman, M., "The Pocket Protector: A New Breast Implant Device", Am. Jour. Cos. Surg., 2004, vol. 21, No. 3, pp. 27-41.

Berman, M., et al., "The Use of Gore-Tex® E-PTFE Bonded to Silicone Rubber as an Alloplastic Implant Material", Laryngoscope, 1986, vol. 96, No. 5, pp. 480-483.

Definition of Breast Implant as defined by Wikipedia: The Free Encyclopedia retrieved from https://en.wikipedia.org/wiki/Breast_implant on Oct. 6, 2015.

Definition of Gore-Tex as defined by Wikipedia: The Free Encyclopedia retrieved from https://en.wikipedia.org/wiki/Gore-Tex on Oct. 6, 2015.

Definition of Polytetrafluoroethylene as defined by Wikipedia: The Free Encyclopedia retrieved from https://en.wikipedia.org/wiki/Polytetrafluoroethylene on Oct. 6, 2015.

Definition of Synovial fluid as defined by Wikipedia: The Free Encyclopedia retrieved from https://en.wikipedia.org/wiki/Synovial_fluid on Oct. 6, 2015.

Definition of Synovial membrane as defined by Wikipedia: The Free Encyclopedia retrieved from https://en.wikipedia.org/wiki/Synovial_membrane on Oct. 6, 2015.

Dodson, B., "Bringing Teflon and silicone together shows promise for medical applications", 2012, retrieved from http://www.gizmag.com/teflon-silicone-binding/23872/ on Oct. 6, 2015.

Edwards, B. F., "Teflon-Silicone Breast Implants", Plast. Reconstr. Surg., 1963, vol. 32, No. 5, pp. 519-526.

Ham, J., et al., "Expanded Polytetrafluoroehtylene Implants in Rhinoplasty: Literature Review, Operative Techniques, and Outcome", Facial Plastic Surgery, 2003, vol. 19, No. 4, pp. 331-339.

"Introducing Patent Pending ITW Teflon Bonded Silicone", Technical Data Sheet, retrieved from http://www.unitedsilicone.com/heatsealsupplies/itwteflonbondedsilicone.aspx on Oct. 6, 2015.

Jin, X., et al., "Joining the Un-Joinable: Adhesion Between Low Surface Energy Polymers Using Tetrapodal ZnO Linkers", Advanced Materials, 2012, vol. 24, No. 42, pp. 5676-5680.

Karlan, M.S., et al., "Potentiation of Infections by Biomaterials: a comparison of three materials", Otalaryngology Head Neck Surg., 1981, vol. 89, No. 4, pp. 528-534.

Mishra, Y. K., e t al., "Versatile Fabrication of Complex Shaped Metal Oxide Nano-Microstructures and Their Interconnected Networks for Multifunctional Applications", KONA Powder and Particle Journal, 2014, No. 31, pp. 92-110.

Steiert, A.E., et al., "Capsular contracture by silicone breast implants: possible causes, biocompatibility, and prophylactic strategies", Med Devices: Evidence and Research, 2013, vol. 6, pp. 211-218.

\* cited by examiner

GORE-TEX COVERED BREAST IMPLANTS TO MINIMIZE CAPSULAR REACTION AND INFECTION WHILE REDUCING PALPABILITY

CROSS-REFERENCE TO RELATED APPLICATIONS

This application claims priority to U.S. Provisional Application No. 62/060,480, entitled "GORETEX COVERED BREAST IMPLANTS TO MINIMIZE CAPSULAR REACTION", filed Oct. 6, 2014, and U.S. Provisional Application No. 62/066,704, entitled "EPTFE IMPLANTS", filed Oct. 21, 2014, which applications are hereby incorporated in their entirety by reference.

BACKGROUND OF THE INVENTION

Implants can be used to augment particular areas of the human body, such as calves, breasts and others. Implantation of implants can be used for reconstructive purposes or cosmetic purposes. For breast implants, reconstructive implantation purposes can include implantation after mastectomy for breast cancer, where a woman has had one or both breasts removed, while cosmetic reasons for implantation can include to change the size, firmness, or shape of the breast or for other aesthetic reasons.

Current breast implants include saline implants and silicone implants. Saline implants can include silicone shells filled with sterile salt water such as saline. Silicone implants can include silicone shells filled with silicone gel. Implantation procedures typically involve a surgeon making an incision under the breast, under the arm or around the nipple and then implanting the implant into a pocket or capsule above or below the chest muscle. The surgeon then closes the incisions with sutures.

Previously contemplated methods involving breast implant devices using Gore-Tex and expanded polytetrafluoroethylene, also known as ePTFE, and Teflon have not been widely implemented for various reasons as described in the prior art but would have many beneficial properties. These reasons are variously described, as follows:

Previous patents that have used ePTFE as an outer layer coating have generally done so in order to create textured surfaces that try to encourage tissue ingrowth from surrounding tissues. U.S. Pat. Nos. 8,647,393; 8,372,423; and 5,779,734 which are incorporated herein in their entirety by reference are examples of such ingrowth embodiments. As described in the stated goal of the U.S. Pat. No. 8,647,393: "[d]isclosed herein are implantable devices coated with microporous surface layers with macrotopographic features that improve bio-integration at the interface of the implantable devices and the surrounding tissue."

A recent non-patent reference states that "[a]fter multiple experimental and clinical trials, there seems to be a strong consensus that the use of textured outer shell surfaces, in comparison with smooth surfaces, is able to decrease the incidence of capsular contracture by disrupting contractile forces around the implant, emphasizing the need for better physical properties than cellular or pharmacological strategies of contracture formation." *Capsular Contracture by silicone breast implants: possible causes, biocompatibility, and prophylactic strategies*, Steiert A E et al, Med Devices (Auckl) 2013; 6:211-218, which is hereby incorporated in its entirety by reference.

Another paper, published in November 1963 and titled *Teflon-Silicone Implants* by Benjamin Edwards, MD described the use of "Teflon felt" over a silicone implant because "[t]he following characteristics of an ideal breast implant are well known to every plastic surgeon. Such an implant . . . should become firmly attached to body tissues." Plastic and Reconstructive Surgery November 1963; Vol. 32, No. 5, pp 519-526, which is hereby incorporated in its entirety by reference. The author further stated that in his opinion "[i]t is most important to have some sort of rough surface on the outside . . . . As we have used here, a layer of Teflon foam."

As described above, the state of the art is that rough outer surfaces are desirable on implants in order to increase capsular formation and promote direct bio-integration of implants with their surrounding tissue. However, as described herein and opposite and distinct from the prior art goals, methods, and devices, it can be beneficial to prevent direct bio-integration between an implant and its surrounding tissue. In such cases, creation of an intima, bursa and synovial fluid environment or combinations thereof, in which an implant is not held in rigid position by a capsule and where an implant may or may not have an outer layer of cellular growth can provide unique and heretofore unknown benefits over the current state of the art.

Further, use of novel materials which have not previously been applied to implants because of their compositions and difficulty in bonding with silicone, are disclosed. Another paper, published in May 2014 and titled *The Pocket Protector: A New e-PTFE Breast Implant Device* by Mark Berman, MD, states that "E-PTFE is considered one of the safest synthetic implant materials. Nonetheless, e-PTFE does not have the elastic properties of silicone rubber and would not serve well as a coating on the implant." Amer. Soc. of Cosmetic Breast Surgery 31$^{st}$ Annual Workshop May 1-4, 2015, which is hereby incorporated in its entirety by reference. As such, the state of the art is that it teaches away from using e-PTFE as a coating on an implant because of its less elastic character than silicone rubber despite its known advantageous properties of being safe. Further, while coupling an ePTFE layer and silicone layer at an interface has been attempted in the past, it has achieved only minimal success without commercial viability, but newer methods of linking, adhering, gluing, or otherwise coupling ePTFE and silicone together can improve bio-acceptance as well as provide numerous other benefits.

Thus, as described herein and different from prior methods and breast implant devices, creation of an exterior implant surface that is not rough or textured and does not promote tissue integration at the implant surface and having the various advantages provided by materials such as ePTFE would be beneficial.

BRIEF DESCRIPTION OF THE DRAWING(S)

Illustrated in the accompanying drawing(s) is at least one of the best mode embodiments of the present invention In such drawing(s).

DETAILED DESCRIPTION OF PREFERRED EMBODIMENTS

The following description of the preferred embodiments of the invention is not intended to limit the invention to these preferred embodiments, but rather to enable any person skilled in the art to make and use this invention. Further, the figures herein are not meant to be limiting based on any scale or size relation illustrated but rather are meant to be example embodiments illustrative of concepts. Although any methods, materials, and devices similar or equivalent to those described herein can be used in the practice or testing of embodiments, the preferred methods, materials, and devices are now described.

The present invention relates to improved methods, systems and implant devices having minimal capsular reaction, infection prevention and reducing palpability along with other benefits. While these methods, systems and devices are particularly suited for breast implants, it should be understood that the disclosure herein is not limited to such environments and can be used in other implantation methods, systems and devices with similar concerns.

Figure 1:
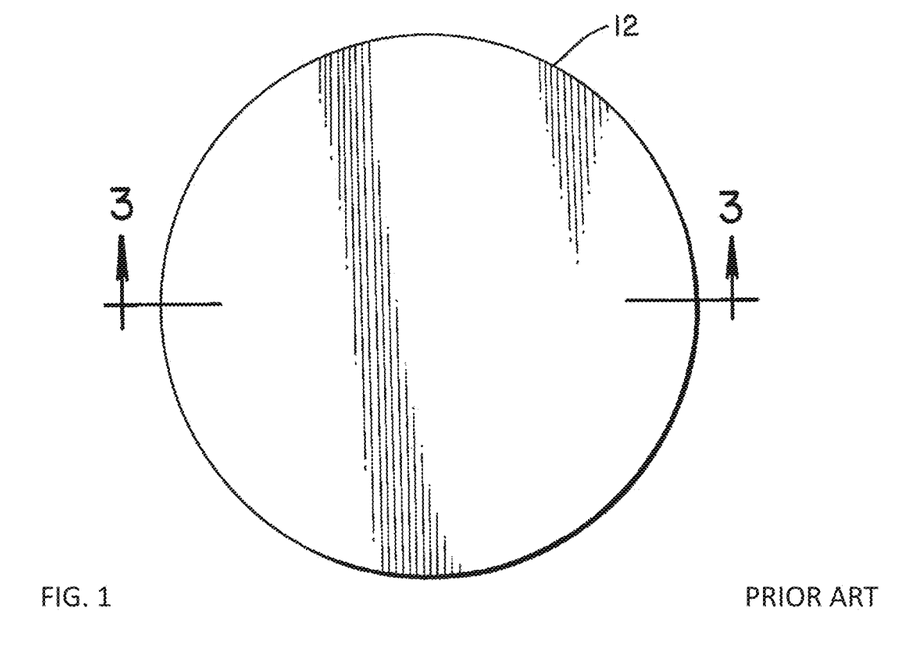
FIG. 1 shows a top view of an example embodiment of a prior art breast implant.

FIG. 1 shows a top view of an example embodiment of a prior art breast implant. In the example embodiment, a breast implant 12 is shown. Breast implants 12 can be silicone implants or saline implants as currently known in the art. As is shown and commonly known, breast implants 12 are generally round, having a substantially standard radial diameter from a center point as viewed from a top down perspective. Breast implants 12, when viewed from a side after implantation (not shown), create a typically natural breast contour which can be round or slightly oblong shape.

Figure 2:
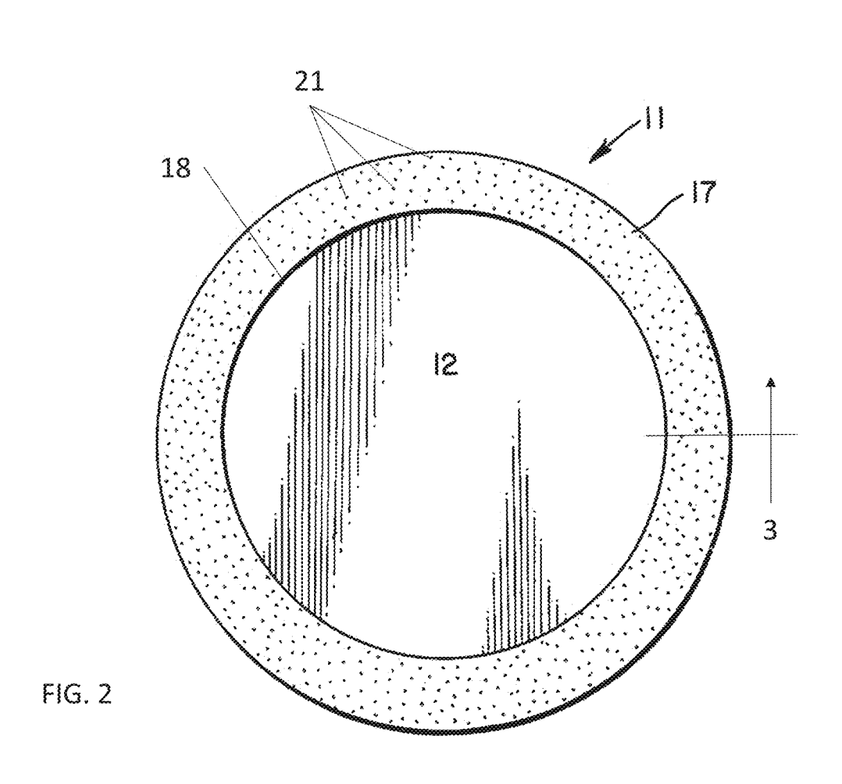
FIG. 2 shows a top view of a cross section of an example embodiment of a breast implant with an ePTFE layer.

FIG. 2 shows a top view of a cross section of an example embodiment of a breast implant 11. In an example embodiment, a breast implant 11 can include an implant 12 having an exterior layer of silicone as is known in the art or later developed, surrounded by an ePTFE (expanded polytetrafluoroethylene, also known as Gore-Tex® by W. L. Gore & Associates, Inc.) layer 17 having a plurality of micropores 21. An interface 18 between implant 12 and ePTFE layer 17 can include mechanical (e.g. see FIG. 4), adhesive (e.g. see FIG. 3), or other coupling means by which the ePTFE layer 17 is adhered to the surface of the implant 12.

Use of ePTFE in the first white, soft, lightweight and covered breast implants can be distinguished from the prior art. Current breast implants are typically clear, can be firm and do not provide an outer covering. Use of ePTFE as an implant covering can provide mental and psychological benefits for patients contemplating surgery since they receive peace of mind in feeling the light weight of the implants and the soft surface that will be in contact with their internal tissues. The white exterior can also resemble a cloud, further allaying some psychological issues.

Coupling ePTFE and Silicone

Connecting, adhering, fastening, joining, or otherwise coupling a silicone rubber shell or silicone gel to one or more ePTFE or Gore-Tex layers has traditionally been a challenge but various new methods and devices are described herein in order to solve these problems. As such, different embodiments of interfaces 18 will be variously described with respect to FIGS. 3-4.

Figure 3:
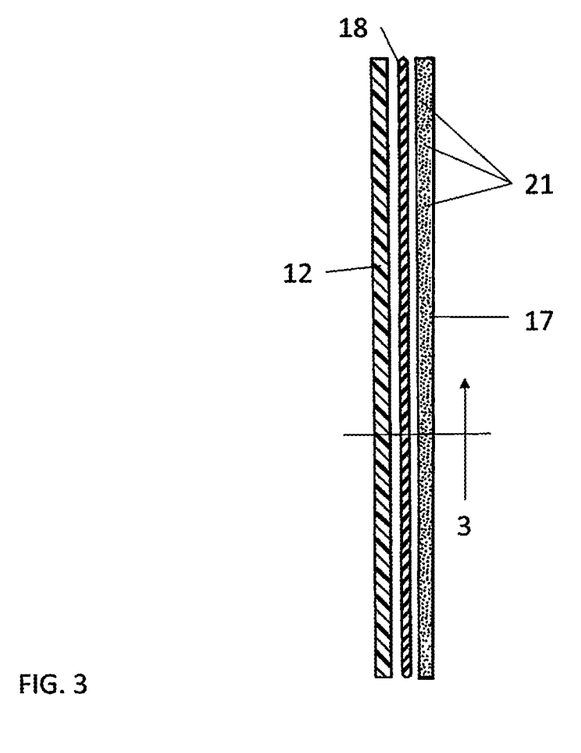
FIG. 3 shows an exploded cross-sectional view of an example embodiment of a breast implant with ePTFE coating and adherence layer, along the plane indicated by the line 3 in FIG. 2.

FIG. 3 shows an exploded cross-sectional enlarged view of an example embodiment of abreast implant with ePTFE coating 17 and silicone layer 12 including an interface 18, along the plane indicated by the line 3 in FIG. 2. Although spaces (not labeled) are shown in FIG. 3 between ePTFE coating 17, interface 18 and silicone layer 12, these are merely to facilitate viewability of the Figure and would be understood by those in the art as being minimal or nonexistent in actual embodiments.

In the example embodiment shown in FIG. 3, interface 18 can be one or more layers or mixtures of chemical glues or adhesives can be used to attach or adhere ePTFE layer 17 and similar layers of compounds to silicone layer 12. In some embodiments, interface 18 can be an alloplastic implant material, an example of which is described by Berman et al. in: "The use of Goretex e-PTFE bonded to silicone rubber as an alloplastic implant material." Laryngoscope (1986): 96(5), pp 4 80-3 which is hereby incorporated in its entirety by reference.

In some embodiments, interface 18 can be a proprietary bonding of ePTFE to Silicone. An example of a PTFE (Teflon) bonded Silicone which is referred to as ITW Teflon Bonded Silicone®, and described in the Technical Data Sheet "Introducing Patent Pending ITW Teflon Bonded Silicone" was developed by ITW United Silicone of Lancaster, N.Y. and which is hereby incorporated in its entirety by reference.

Additional gluing methods and treatments are described in an as yet unpublished Cornell University Alabi technology U.S. patent application Ser. No. 14/830,374, which is hereby incorporated in its entirety by reference. These methods and treatments involve the use of a specialty polymer with orthogonal allyl acrylamide building blocks with R groups that alternately adhere to silicone with other R groups that adhere to ePTFE.

PTFE, also known as Teflon, has some similar characteristics to ePTFE. A method of attaching, bonding or otherwise coupling PTFE (Teflon) to silicone while also reducing problematic issues with seams can be found in the patent application PCT Publication WO/2014/116490 A1, titled "Silicone E-spun PTFE Composites" and filed Jan. 16, 2014, invented by Ballard et al and applied for by Zeus Industrial Products, Inc. of Orangeburg, S.C., which is hereby incorporated in its entirety by reference. As described, electrospin porous, polymeric components, such as PTFE, can be created around a silicone component and make a composite of PTFE that is adhered to silicone.

Figure 4:
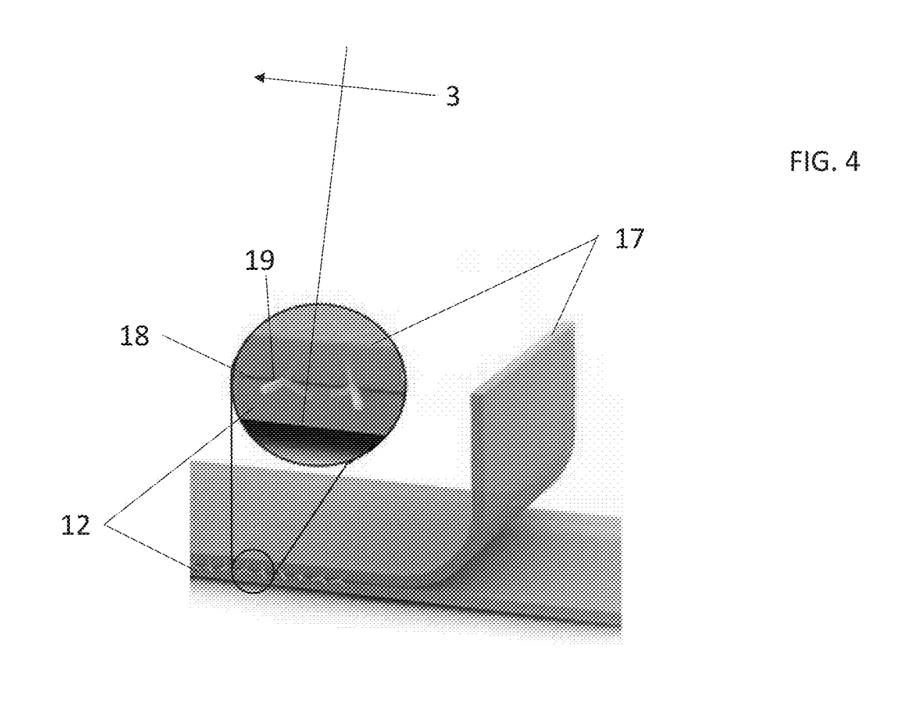
FIG. 4 shows a cross-sectional view of an example embodiment of a breast implant with an ePTFE with mechanical adhering.

FIG. 4 shows an exploded cross-sectional view of an example embodiment of a breast implant surface with an ePTFE coating 17 and silicone layer 12 including an interface 18 with a plurality of mechanical coupling elements 19, along the plane indicated by the line 3 in FIG. 2. As shown in the example embodiment, mechanical linking of ePTFE and Gore-Tex can be accomplished using mechanical coupling elements 19 or otherwise structural components which can have caltrop or tetrapod shapes and can have varied orientations in different embodiments. In some embodiments, distribution and orientation of mechanical coupling elements 19 can be standardized or repetitive. Various additional features of mechanical coupling elements 19 are contemplated include hooks, fasteners, protrusions, and others. In some embodiments both adhesives and mechanical components 19 can be used at interface 18 and in some embodiments mechanical components 19 can be treated with adhesives.

In various embodiments, mechanical linking of PTFE (Teflon) or ePTFE (Gore-Tex) and silicone can include application of zinc oxide nanocrystals (ZnONC) or other materials with caltrop or tetrapod shapes that link opposing surfaces of an ePTFE layer and a silicone layer. In an embodiment, the mechanical components 19 can be placed between ePTFE layer 17 and silicone layer 12 before applying heat to one or both layers at the same time. This can cause the mechanical components 19, also known as nano-structure anchors, to imbed at least partially into both layers, thus holding the two layers together. These can have metal oxide nano-, micro- or nano-micro-structures which can "join two extremely difficult-to-join polymer layers, namely poly(tertafluorethylene) (PTFE) and cross-linked poly(dimethylsiloxane) (PDMS)," as described in an article by Dodson, published Aug. 26, 2012 on www.gizmag.com titled: "Bringing Teflon and silicone together shows promise for medical applications," which is hereby incorporated in its entirety by reference. See: http://www.gizmag.com/teflon-silicone-binding/23872/.

In some embodiments, complex shaped metal oxide nano-structures can create interconnected networks which can be applied to surfaces for linking materials. An example is described by Mishra et al in: "Versatile Fabrication of Complex Shaped Metal Oxide Nano-structures and Their Interconnected Networks for Multifunctional Applications," Kona Powder and Particle J., No. 31, (2014) pp. 92-110, which is hereby incorporated in its entirety by reference.

In some embodiments, adhesion between low surface energy polymers can be accomplished using tetrapodal ZnO components. An example is described by Jin et al in: "Joining the un-joinable: Adhesion between low surface energy polymers using tetrapodal ZnO linkers," Adv. Mater., Vol. 24, (2012) pp. 5676-5680 which is hereby incorporated in its entirety by reference.

Figure 5:
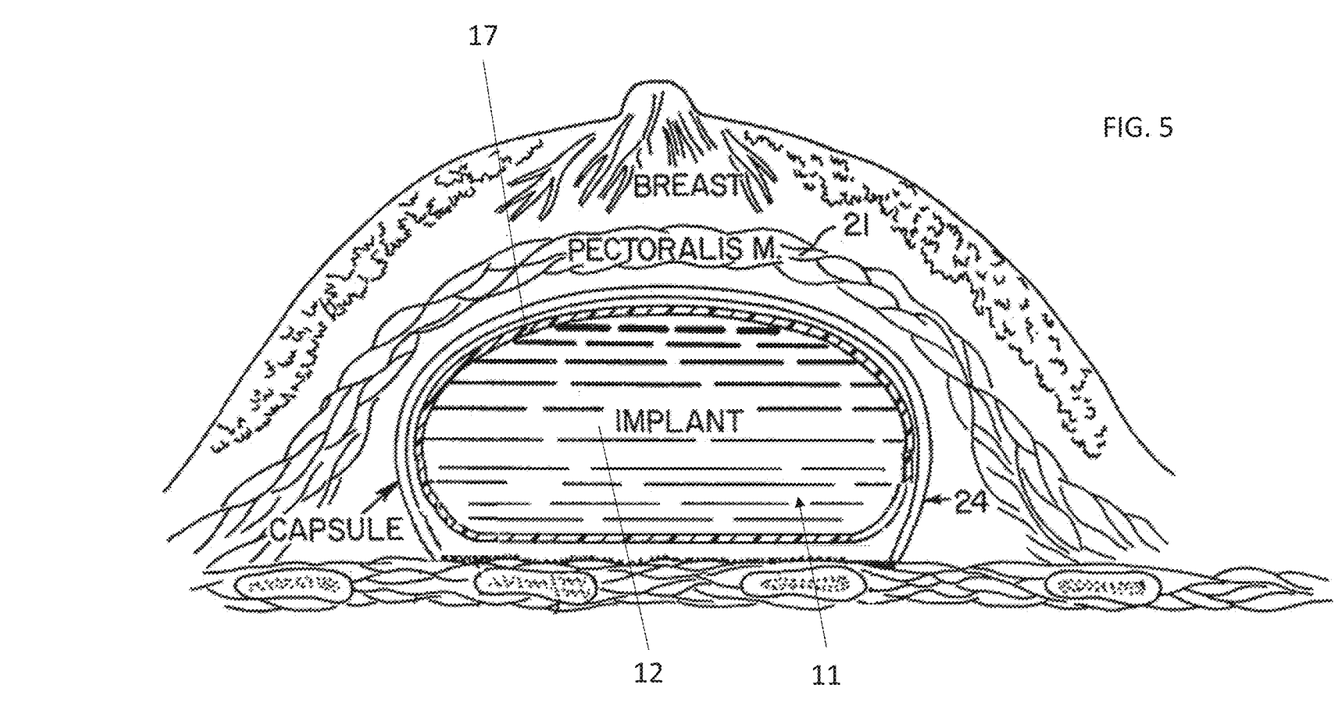
FIG. 5 shows a side cross-sectional view of a fibrous capsule in conjunction with an example embodiment of a breast implant just after implantation and before development of an intima.

FIG. 5 shows a side cross-sectional view of a fibrous capsule 24 in conjunction with an example embodiment of a breast implant 11 having an ePTFE coating 17 and silicone layer 12 just after implantation and before development of an intima.

Benefits and Uses of ePTFE implants

The use of one or more ePTFE layers 17 as shown in FIGS. 2-5 or similar surfaces, can serve as a soft, pliable, microporous (e.g. micropores 21 shown in FIGS. 2-3), smooth outer layer of a breast implant or other implant, providing numerous beneficial properties over the prior art as described herein. In some embodiments, an entire implant can be comprised of ePTFE (not shown) as opposed to merely using it as a coating as shown in FIGS. 2-5. In other embodiments (e.g. FIGS. 2-5), an ePTFE implant can be an implant with a silicone surface, known in the art as a polysiloxanes implant and filled with a silicone gel or saline, where the silicone surface can be smooth or textured in various embodiments and has a constant or varying thicknesses of an outer layer of ePTFE or similar coating applied to the silicone surface at an interface.

Micro-Structures and Pre-Treatments

Although smooth to human touch, ePTFE or Gore-Tex has a microporous framework with a porosity of about 10-30 microns, averaging about 22 μm in diameter as described in *ePTFE Implants in Rhinoplasty: Literature Review, Operative Techniques, and Outcome*, Ham J., Miller P. Facial Plastic Surgery 2003; Vol. 19, No. 4, which is hereby incorporated in its entirety by reference. These microporous framework characteristics, along with non-stick or electronegative and favorable biocompatible properties of ePTFE can help ePTFE resist tissue ingrowth which can be beneficial in various embodiments. Tissue ingrowth can cause tissue adherence to an implant surface of prior art implants and can thwart any postoperative implant movements. However, application of at least one ePTFE coating layer can prevent this tissue adherence, allowing for postoperative implant movements by a patient, nurse, surgeon, doctor or other healthcare worker. These postoperative implant movements can provide numerous benefits, at least one of which is that this can result in the forming of a post-operative scar capsule with a larger three-dimensional structure than the actual physical three-dimensional size of the implant with the ePTFE coating.

In various embodiments herein, micro-structured gaps, as described above and also referred to herein as micro-pores (e.g. micro-pores 21 in FIGS. 2-3), in ePTFE layers of an ePTFE coated or ePTFE implant can also serve as reservoirs for various chemicals in the surface of the ePTFE. These chemicals, along with the soft, smooth characteristic of ePTFE, can serve to optimize biological acceptance of the implant and minimize risk of capsular contracture which will be further described below.

In some embodiments, delivery chemicals or substances implanted, stored or otherwise located in the micro-structured gaps of a treated ePTFE implant can assist in implant delivery or other implantation procedures by allowing for and enabling the use of a more slippery surface than currently available. This can be accomplished by a manufacturer applied or pre-operative treatment and maintenance a surface chemical or peri-implant space material in the micro-pores of the ePTFE surface, unlike the current state of the art that provides only for secondary treatments to implant surfaces. This pre-treatment or primary treatment can also encourage movement of the implant within an implant capsule and thus provide for the benefits of larger post-operative capsule formation, the benefits of which were described above.

Additionally or alternatively, in some embodiments, chemicals or other substances that can act to discourage immediate and prolonged tissue adherence can be applied and maintained in the micro-structured gaps. These surface chemicals or peri-implant space materials can function similar to several chemicals, substances or materials which are known in the art but are not integrated with a physical surface of an implant currently because they are merely applied as a secondary treatment to an implant surface. Examples of these secondary treatments of implant surfaces can include: a) a hydrophilic inner layer of a Keller funnel; b) a lubricating material in refresh drops, such as carboxymethylcellulose sodium/glycerin/polysorbate 80; and c) a synthetic synovial fluid. These secondary treatments as referred to herein are treatments applied to implants that typically occur at or near the time of implant delivery or implantation. As would be understood in the art, the current ePTFE pre-treated or primary treated surface which is microporous and can maintain one or more chemicals or substances can also be used in conjunction with any of the secondary treatments as well, in order to provide additional benefits.

In some embodiments, in order to reduce or eliminate capsular contracture and associated morbidity that capsular contracture can cause, additional or alternatively applied surface chemicals or peri-implant space materials can include at least: a) antibiotics, such as Rifampin and others; b) calcium channel blockers, such as Verapamil and others; c) Vitamin E, including the synthetic form alpha-tocopherol; d) Methylprednisolone and others; and e) others. Surface chemicals or peri-implant space materials can also optimize conditions for cellular adhesion and growth on an outer surface of implants for creation of an intima, bursa, and synovial environment as opposed to integration by the tissue around the implant. These chemicals, substances or materials can include one or more of: a) Synovial fluid-like material; b) Pre-treatment with alcohol or c) others.

ePTFE reservoirs in the form of micropores can allow chemicals to be layered in and on the ePTFE surface, especially in embodiments where a layer of ePTFE of an implant is relatively thick. In an example embodiment, an external substance layer can be coated on an outer, external ePTFE implant surface to help optimize slippery characteristics of the ePTFE implant as would be beneficial in the first few days or weeks after an implantation procedure. This coating layer can dissipate over time and be appropriately absorbed by the body.

In an example embodiment, a secondary or intermediate layer can be presoaked by a surgeon or otherwise implanted in the ePTFE reservoirs or surface by a manufacturer, typically prior to the external substance layer. In various example embodiments, the secondary or intermediate layer can include an antibiotic layer or inhibitory layer which can serve to prevent or inhibit bacterial infection or infections caused by other biological pathogens.

Similarly, a tertiary layer or other deeper layer or layers can be applied prior to the secondary or intermediate layers and external layers. The tertiary layer or deeper layers can include chemicals, substances and materials which can be expressed, released or administered more slowly, over a longer time or at a delayed time and can assist with cellular adhesion in order to help create a beneficial intima as a bursa or synovial type environment.

Application or implantation of chemical, substance or material layers can be accomplished while accounting for particular timing, interaction, heating, cooling or other chemical, substance or material specific concerns taken into consideration during the pre-treatment or primary treatment process, as would be understood by those in the art.

Capsular Issues Including Tissue Adherence through Contracture and Microbial Growth A thick or contracting scar capsule around an implant can be an undesirable side effect of implantation because it can cause numerous problems including: pain, hardness, and significant distortion of external anatomy. Additionally it can cause electrical disturbance and decreased lifespan of wires associated with internal defibrillators and pacemakers. As such, an implant with at least one ePTFE surface can beneficially minimize tissue adherence problems associated prior art implants including capsular contracture. Microporous ePTFE surfaces can provide smooth, soft and biocompatible surfaces that can move easily in a capsular 'pocket' after implantation and thus produce a thin capsule size which can be larger in physical volume size without increased thickness of capsular walls.

One of the main proposed etiologies or medical causes of capsular contracture is microbial contamination. In various embodiments, ePTFE micropores can provide an inhibitory effect on microbial contaminant growth with or without antibiotic soaking and thus can be correlated with lower capsular contracture rates. In an example embodiment, a solution of Fluorocarbons can be applied to an ePTFE layer of an implant and thus inhibit the creation of a biofilm or other undesired bacterial layer or frank infection. Fluorocarbon coated implants have been described by Karlan et al in *Potentiation of Infections by Biomaterials: a comparison of three materials*. Otolaryngol Head Neck Surg. 1981; 89:528-534, which is hereby incorporated in its entirety by reference, as having a significantly decreased infection rate when compared to silicone.

In some embodiments, ePTFE or Gore-Tex layers can also reduce problems associated with capsular contracture using other mechanisms. Microporosity can be optimized for particular facilitating environments in which the optimized microporous ePTFE layers can allow for topical cellular growth outward or around the ePTFE implant in different amounts and at different rates. This is in direct contrast with 'tissue integration' in prior art implants in which the tissue grows into and fixes a location of the implant. Thus, an ePTFE implant can develop a monocellular or multicellular 'intima' (not shown) over the ePTFE surface of the implant. Once this intima is formed, the relationship of the implant with the capsule can perform similarly to performance of naturally occurring biological environments in which a bursa or synovial type environment has two biological membranes opposing each other. In the ePTFE implant embodiments including two biological membranes, one can be a biological membrane capsule and one can be a biological membrane intima around the ePTFE implant. As has been contemplated but heretofore unaccomplished in the art, this type of environment can be a beneficial structural environment: "[i]nterestingly, the macroscopically smooth-surface implant also presents with a rippled microscopic texture on the surface, which might increase the formation of a synovial-type epithelium, experienced in fibrotic breast capsules." *Capsular Contracture by silicone breast implants: possible causes, biocompatibility, and prophylactic strategies*, Steiert A E et al, Med Devices (Auckl) 2013; 6:211-218, which is hereby incorporated in its entirety by reference.

These two biological membranes opposing each other can be considered two disconnected structures which are not otherwise rigidly connected or coupled. This differs from the common view in the current state of the art in which implants are frequently described as optimally being firmly attached to body tissues, otherwise known as having 'tissue integration.' Similar intimas can be found along inner lumens of aortic ePTFE or Gore-Tex implants.

As known in various medical arts, creation of an intima can be described as follows: "[a]s a rule, host cells do not adhere directly to the surface of synthetic implanted materials. Extracellular proteins and proteoglycans form a substrate to which the cells attach. Interactions with cell membrane receptors furnish the linkage for cellular attachment to adsorbed extracellular matrix proteins on implant surfaces. The predominant cells that attach to the protein layer are the fibroblasts. The fibroblasts lay down immature collagen over the matrix on the implant and into the interstices of porous implant. This ingrowth of collagen fibers provides the framework for subsequent cellular adhesion," as described in: *ePTFE Implants in Rhinoplasty: Literature Review, Operative Techniques, and Outcome*, Ham J., Miller P. Facial Plastic Surgery 2003; Vol. 19, No. 4, which is hereby incorporated in its entirety by reference. This is different than the prior art teachings in which the actual surrounding tissue is desired or encouraged to grow into or 'integrate' into an outside layer of an implant. In some embodiments, some cells can 'adhere' or otherwise grow or couple to an exterior ePTFE layer of an implant, forming an essential 'intima'.

ePTFE Implants and Silicone Problem Reduction

Additionally, an ePTFE implant can be safer from a medical standpoint for users receiving it as an implant. One or more ePTFE layers adhered to a silicone implant can serve to create an additional barrier to leakage of silicone gel out of a silicone implant when used with a silicone implant.

Thus, users can have a reduced chance of negative tissue reaction due to failure of a silicone implant than with traditional silicone implants.

In some embodiments, one or more layers of ePTFE can greatly reduce any penetration of silicone into surrounding tissue since silicone particles are unable to pass through an ePTFE layer because the micropores in an ePTFE layer are smaller in diameter than the diameter of silicone particles. This can reduce or eliminate problems with silicone particles and silicone-laden macrophages in a capsular environment. Some of these problems are described by Prantl et al, including increased capsular thickness as correlated with an increase in silicone particles and silicone-laden macrophages in a capsule. *Capsular Contracture by silicone breast implants: possible causes, biocompatibility, and prophylactic strategies*, Steiert A E et al, Med Devices (Auckl) 2013; 6:211-218, which is hereby incorporated in its entirety by reference. Thus, since thickening of a capsule is not desirable in many example embodiments described herein and an ePTFE layer will reduce or inhibit their ability to implant in tissue surrounding the implant, the ePTFE layer can be desirable.

Other Advantages

An ePTFE or Gore-Tex covering over silicone implants can also provide a more natural 'feel,' more similar to a natural breast than current silicone gel implants without ePTFE. This advantage occurs by providing a softer cushion for finger touch due to the soft nature of ePTFE compared to silicone while also minimizing creation and feel of silicone rubber shell undulations, folding and rippling.

ePTFE covered silicone implants can be lighter in weight than current, fully silicone implants of similar size, especially in embodiments where a thicker layer of ePTFE covering is provided. This is due to the fact that the density of ePTFE can be as low as <0.1 gm/ml, with a porosity of 96%, while the density of a silicone gel implant is about 0.97 gm/ml and the specific gravity of saline is 1 gm/ml. Thus, the density of a quantity of ePTFE can be at least 9.7% less dense than a similar quantity of silicone and at least 10% less dense than a similar quantity of saline. The effect of providing implants with ePTFE that are lighter that other implants can make the implants easier to carry for most patients, decrease neck and shoulder pain sometimes associated with heavier breasts due to implants, and decrease breast ptosis and associated inframammary intertrigo.

The preceding described embodiments of the invention are provided as illustrations and descriptions. They are not intended to limit the invention to precise form described. Other variations and embodiments are possible in light of above teachings, and it is thus intended that the scope of invention not be limited by this Detailed Description, but rather by Claims following.

What is claimed is:

1. An improved breast implant, comprising:
  an ePTFE layer comprising:
    a smooth exterior surface;
    an interior surface; and
    a plurality of micro-pores;
  a breast implant core, comprising:
    a filler substance; and
    a silicone layer operable to contain the filler substance and having an exterior surface;
  a mechanical interface, comprising:
    a plurality of mechanical coupling elements, at least some of which have caltrop shapes,
    wherein the mechanical interface is located between and couples the interior surface of the ePTFE layer and the exterior surface of the silicone layer; and
  at least one additional substance stored in at least one of the micro-pores, operable to cause an implantation effect associated with the breast implant.

2. The breast implant of claim 1, wherein at least some of the mechanical coupling elements have a tetrapod shape.

3. The breast implant of claim 1, further comprising:
  an adhesive interface located between and coupling the interior surface of the Pete layer and the exterior surface of the silicone layer.

4. The breast implant of claim 1, wherein the mechanical coupling elements further comprise:
  metal-oxide crystal structures.

5. The breast implant of claim 4, wherein the metal-oxide crystal structures are zinc-oxide nanocrystals.

6. The breast implant of claim 1, further comprising:
  an alloplastic material interface located between and coupling the interior surface of the Pete layer and the exterior surface of the silicone layer.

7. The breast implant of claim 1, further comprising:
  a polymer interface with orthogonal allyl acraylamide building blocks having R groups located between and coupling the interior surface of the ePTFE layer and the exterior surface of the silicone layer.

8. The breast implant of claim 7, wherein the R groups alternately adhere to the silicone layer and the ePTFE layer.

9. The breast implant of claim 1, wherein the effect of the additional substance prevents tissue adherence to the breast implant after implantation.

10. The breast implant of claim 1, wherein the effect of the additional substance stimulates cellular growth of an intima around at least a portion of the breast implant after implantation.

11. The breast implant of claim 1, wherein the additional substance further comprises:
  vitamin E or alpha-tocopherol.

12. The breast implant of claim 1, wherein the additional substance further comprises:
  a lubricating material.

13. The breast implant of claim 1, wherein the additional substance further comprises:
  a synthetic synovial fluid.

14. The breast implant of claim 1, wherein the additional substance further comprises:
  a hydrophilic material.

15. The breast implant of claim 1, wherein the additional substance further comprises:
  an antibiotic.

16. The breast implant of claim 1, wherein the additional substance further comprises:
  a calcium channel blocker.

17. The breast implant of claim 1, wherein the additional substance further comprises:
  fluorocarbon.

* * * * *